United States Patent [19]

Schmolka

[11] Patent Number: 4,534,959
[45] Date of Patent: Aug. 13, 1985

[54] AEROSOL GEL

[75] Inventor: Irving R. Schmolka, Grosse Ile, Mich.

[73] Assignee: BASF Wyandotte Corporation, Wyandotte, Mich.

[21] Appl. No.: 524,985

[22] Filed: Aug. 22, 1983

[51] Int. Cl.$^3$ ............................................... A61K 9/00
[52] U.S. Cl. ........................................ 424/45; 424/78; 514/944
[58] Field of Search ..................... 424/45, 78

[56] References Cited

U.S. PATENT DOCUMENTS

| | | | |
|---|---|---|---|
| 2,674,619 | 4/1954 | Lundsted | 260/485 |
| 2,677,700 | 5/1954 | Jackson et al. | 260/488 |
| 2,979,528 | 4/1961 | Lundsted | 260/584 |
| 3,476,853 | 11/1969 | Jatul et al. | 424/45 |
| 3,639,575 | 2/1972 | Schmolka | 424/78 |
| 3,740,421 | 6/1973 | Schmolka | 424/65 |
| 3,751,562 | 8/1973 | Nichols | 424/45 |
| 4,293,542 | 10/1981 | Lang | 424/47 |

FOREIGN PATENT DOCUMENTS 1444334 7/1976 United Kingdom .

OTHER PUBLICATIONS

Chemical Abstracts 82: 45617r (1975), Veltman.

Primary Examiner—Leonard Schenkman
Attorney, Agent, or Firm—Bernhard R. Swick

[57] ABSTRACT

A pressurized composition in an aerosol container and adapted to form a spray upon release of pressure therefrom which composition is a liquid inside the container and forms a gel on contact with living tissue comprising water, propellant and a polyoxyethylene-polyoxypropylene copolymer. The preferred composition may advantageously include a skin treating agent, and conventional adjuvants.

10 Claims, No Drawings

AEROSOL GEL

BACKGROUND OF THE INVENTION

1. Field of the Invention

The present invention relates to a sprayable aerosol composition which is a liquid in the aerosol container and forms a gel upon application to the skin.

2. Prior Art

The preparation of aqueous gels employing as gelling agents polyoxyethylene-polyoxypropylene block copolymers is well known to those skilled in the art and is taught in several patents including U.S. Pat. No. 3,740,421. Such gels may be advantageously employed in the preparation of topically applicable cosmetic and pharmaceutical compositions. It is also known in the art to apply such compositions by the use of aerosol-type containers. However, filling an aerosol container with a gel presents problems.

U.S. Pat. No. 3,751,562, issued Aug. 7, 1973, to Nichols, discloses an aerosol gel formulation employing an oxyethylated fatty alcohol, mineral oil, iodine and water.

U.S. Pat. No. 4,293,542, issued Oct. 6, 1981, to Lang et al, discloses aerosol formulation which can be an aqueous gel containing oxyethylated fatty alcohols and a gel-forming agent and, as an essential component, a pyridine derivative.

British Pat. No. 1,096,357 discloses an aerosol gel comprising a partial fatty acid soap of a polyvalent metal hydroxide and a nonpolar oil along with propellants.

In U.S. Pat. No. 3,476,853, a sprayable composition for use as a dressing, including a film-forming material, an opacifying material, at least one medicament, a solvent and a gaseous propellant, is disclosed. The fluid dressing or bandage is applied by spraying the fluid dressing from a closed pressure-resistant container by the expansion of a normally gaseous propellant in liquid state. The patent discloses a means for applying a protective opaque film which is immediately dry to the touch when applied from a distance of 4 to 6 inches. This provides a simulated bandage.

British Pat. No. 1,444,334 discloses an aerosol gel composition which may be employed as a shaving cream composition and which contains as a gelling agent a polyoxypropylene-polyoxyethylene block copolymer. The composition also includes a water-soluble soap. This patent is concerned with the problem of expelling a gel from an aerosol container and particularly avoiding cavitation around the dip tube as can be seen from column 2 thereof. Accordingly, the compressed gas or liquified gaseous propellant is required to be substantially insoluble in the gel so that it can act in the manner of a piston to force the gel from the container without cavitation.

Copending U.S. patent application Ser. No. 513,439 discloses an aerosol gel burn treatment composition which is a liquid in the aerosol can and forms a gel upon application to the skin. This application requires as an essential component a volatile solvent in addition to the propellant.

SUMMARY OF THE INVENTION

The cavitation problem discussed in British Pat. No. 1,444,334 as well as filling problems are overcome in accordance with the instant invention by the use of a pressurized composition which may be sprayed from an aerosol container and which is liquid inside the container and forms a gel on contact with living tissue such as in the topical application of cosmetics, pharmaceuticals, shaving creams, etc. Also the need for a volatile solvent as an additional component is eliminated. This is accomplished by the combination of water, propellant and certain polyoxyethylene-polyoxypropylene block copolymers. Generally the composition contains at least one skin treating agent, such as cosmetics, pharmaceuticals, shaving cream components, burn tretment agents, etc., in an effective amount. By the proper selection of the polyoxyethylene-polyoxypropylene block copolymer, and water/copolymer ratio the composition would be a liquid at ambient temperature (20° C. to 25° C.) and would form a gel on being exposed to body heat at atmospheric pressure. Such composition would have a minimum water-to-copolymer ratio of 4.5:1, a molecular weight for the polyoxypropylene hydrophobe of 3250 to 7500 and the oxyethylene groups constitute 45 to 90 percent of the total weight of the copolymer.

Where the polyoxyethylene-polyoxypropylene block copolymer is outside these ranges for hydrophobe molecular weight and/or the water copolymer ratio is less than 4.5:1 a propellant which is also a solvent is incorporated in the composition which evaporates upon contact with body heat whereby the liquid becomes a gel. The use of the propellant which is also a solvent extends the hydrophobe molecular weight and water:copolymer ratio ranges. In this embodiment the polyoxyethylene-polyoxypropylene block copolymer may have a molecular weight of the polyoxypropylene hydrophobe of from about 2250 to 7500 and the oxyethylene groups constitute 45 to 90 percent of the total copolymer weight.

DESCRIPTION OF THE PREFERRED EMBODIMENTS

One embodiment of the aerosol composition of the instant invention comprises by weight about 45 to 90 percent water, about 3 to 50 percent propellant, about 7 to 20 percent of the polyoxyethylene-polyoxypropylene copolymer, 0 to about 10 percent, preferably about 0.05 to 5 percent, of a skin treatment agent, and 0 to 20 percent, preferably about 1 to 5 percent adjuvants.

The polyoxyethylene-polyoxypropylene block copolymer of use in the invention is a cogeneric mixture of conjugated polyoxyethylene-polyoxypropylene compounds corresponding to the following formula:

$$Y[(C_3H_6O)_n(C_2H_4O)_mH]_x \quad (I)$$

wherein Y is the residue of an organic compound having from about 1 to 6 carbon atoms and containing x reactive hydrogen atoms in which x has a value of at least about 1, n has a value such that the molecular weight of the hydrophobe base is about 2250 to 7500 and m has a value such that the oxyethylene chains constitute about 45 to 90 weight percent of the compound. Falling within the scope of the definition for Y are, for example, propylene glycol, glycerine, pentaerythritol, trimethylolpropane, ethylene diamine and the like. The oxypropylene chains optionally, but advantageously, contain small amounts of oxyethylene and oxybutylene groups and the oxyethylene chains also optionally, but advantageously, contain small amounts of oxypropylene and oxybutylene groups. These compositions are more particularly described in U.S. Pat. Nos. 2,677,700, 2,674,619 and 2,979,528 which are incorporated herein by reference.

Nonionics to which this invention is particularly applicable are those wherein Y is propylene glycol, and the resulting formula is:

$$HO(C_2H_4O)_m(C_3H_6O)_n(C_2H_4O)_mH \qquad (II)$$

wherein n has a value such that the molecular weight of the hydrophobe is about 2250 to 4500 and m is the same as in formula (I) above.

Other nonionics of particular value are those where Y is the residue of ethylene diamine and the resulting formula is:

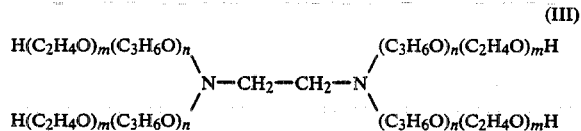
(III)

wherein n has a value such that the molecular weight of the hydrophobic box is about 3500 to 7500 and m is the same as in formula (I) above.

A composition which is a liquid inside the container and forms a gel on contact with living tissue may be achieved by use of the copolymer as defined above and a minimum water/copolymer weight ratio of 4.5:1. There is no maximum water/copolymer ratio other than the limits of the ranges set forth above. To achieve this objective, the polyoxyethylene-polyoxypropylene block copolymers, as described above, should have a hydrophobe molecular weight of from about 3250 to 7500 and the oxyethylene groups should constitute about 45 to 90 percent of the total weight of the compound. Such copolymers when used with a minimum 4.5:1 water/copolymer ratio are liquid systems at ambient temperature and gel when heated by contact with the skin of a mammal.

The propellants can be any one or a blend of the following as examples: propane, isobutane and other petroleum distillates, nitrogen, carbon dioxide, methylene chloride, vinyl chloride, dimethyl ether, methylethyl ether, and fluorochlorohydrocarbons. The latter include Freon 115 pentafluorochloroethane and Freon C-318, octafluorocyclobutane. By selection of a propellant in which the composition is soluble, generally the water soluble propellants, a more broadly defined copolymer may be emplyed and the water/copolymer ratio may be less than 4.5:1 with the overall water content ranging from about 35 to 90 percent and the copolymer content ranging from about 7 to 25 percent.

In such cases the polyoxyethylene-polyoxypropylene block copolymer could have a hydrophobe molecular weight of about 2250 to 7500 and contain oxyethylene groups in amount of about 45 to 90 percent of the total weight of the compound.

Other components of the gel composition of the instant invention would depend on the use of the gel. In many cases it would contain at least one skin treating agent which, when included, would generally be in an amount of about 0.05 to 10 percent by weight. For example, for a shaving cream application the polyoxyethylene-polyoxypropylene block copolymer may serve as the agent for wetting the chin and the beard whereby an additional agent would not be needed. If a high-foaming oxyalkylene copolymer is selected which has a molecular weight of the polyoxypropylene hydrophobe of about 2250 to 2800 and a percentage of oxyethylene groups of about 45 to 80, it would serve as a foaming agent.

If the polyoxyethylene-polyoxypropylene copolymer is a low-foaming copolymer the preferred shaving cream may also contain a foaming agent which may be nonionic, anionic or amphoteric. Nonionics include high-foaming oxyalkylene copolymers and the anionics include sodium lauryl sulfate and lauryl ether sulfates. The propellant may also serve as a foaming agent eliminating the need for an additional foaming agent. Such foaming agent would be included in amount of about 0.1 to 2.0 percent by weight.

A burn treatment composition may include one or more medicaments. The burn treatment medication may be any water-soluble or water-insoluble salt as well as other drugs conventionally used for treatment of burns. Suitable salts would include the nitrates, lactates, acetates, sulfadiazine and other salts of silver or other heavy metals. Antibiotics may also be used such as bacitracin, neomycin, erythromycin, streptomycin, paramycin, bacteriostats such as garamycin, wound healing agents such as piracetam, aloe vera, and other compositions and compounds normally used to speed up burn healing. In general, the composition would contain from about 0.05 to 5.0 percent by weight of the burn treatment medication.

While a medicament is often useful, protection of the burn or wound can be accomplished without the inclusion of a medicating agent the gel forming as a result of the heat of the patient's skin when used for burn applications protecting the burn or wound by itself.

Many and various adjuvants are generally also included in these gels depending on the application for the gel. Other components could include proteins, amino acids, electrolytes and other adjuvants normally found in body fluids. Humectants, such as propylene glycol or glycerine, may also be included. Further adjuvants could include silicone oils. Also, other adjuvants which impart further desired qualities to the skin may be incorporated in the compositions of the invention, e.g., skin fresheners or lather stabilizers or the like such as lanolin or its derivatives, lecithin, higher alcohols, dipelargonate esters or ethers, coconut oil and other fatty esters and mixtures thereof may generally be used in minor proportions. Furthermore, coloring materials such as dyes and perfumes may be used, if desired. The amount of such adjuvants would range from 0 to about 20 percent by weight and preferably from about 1.0 to 5.0 percent by weight.

The following examples are included to further illustrate the present invention. Unless otherwise stated throughout the application, all parts and percentages are by weight and all temperatures are in degrees centigrade.

EXAMPLE 1

A concentrate is prepared from 90 parts water and 20 parts of a polyoxyethylene-polyoxypropylene block copolymer of the type shown in formula (II) above, designated herein as copolymer #1, having a polyoxypropylene hydrophobe molecular weight of 4000 and containing oxyethylene groups in the amount of 70 percent of the total weight of the copolymer. Sixty-five parts of this concentrate are placed in an aerosol container and 35 parts of Freon 115 propellant added through the valve. The contents are shaken and when sprayed onto a patch of human skin form a coating. This becomes a foamy gel as the propellant evaporates.

EXAMPLE 2

Ninety-five parts of a solution comprising 14.0 parts of a copolymer, designated herein as copolymer #2, 63 parts water and 18 parts glycerine are placed in an aerosol container similar to that described in Example 1. The container is pressurized and sealed with a valve and 5 parts of dimethylether propellant added to the aerosol container through the valve.

Copolymer #2 is a polyoxyethylene-polyoxypropylene bock copolymer of the type shown in formula (II) above having a polyoxypropylene hydrophobe molecular weight of 2250 and containing oxyethylene groups in amount of 50 percent of the total weight of the molecule. When sprayed from the aerosol container onto a patch of a human skin, a coating forms which becomes a foamy gel as the propellant evaporates.

EXAMPLE 3

Example 1 is repeated substituting for copolymer #1 a polyoxyethylene-polyoxypropylene copolymer of the type shown in formula (III) above, referred to herein as copolymer #3. This copolymer has a hydrophobe molecular weight of about 7000 and the oxyethylene groups are about 80 percent by weight of the total molecule. When sprayed from the aerosol container onto the a patch of human skin, a coating forms which becomes a foamy gel as the propellant evaporates.

EXAMPLES 4–8

Five solutions are made up from all the components excluding the propellants of each of the example compositions set forth below and each placed in its individual aerosol container. The container is sealed with a valve and the respective propellant added through the valve. The contents of each when shaken and sprayed onto the face of an individual needing a shave forms a coating which becomes a foamy gel as the propellant evaporates. This gel has good shaving characteristics and does not irritate the skin. The compositions are as follows:

EXAMPLE 4

| | |
|---|---|
| 16 | Copolymer #1 |
| 3 | Glycerine |
| 1 | Lauric Diethanolamide |
| 60 | Water |
| 20 | Dimethyl Ether (Propellant) |
| 100 | |

EXAMPLE 5

| | |
|---|---|
| 14 | Copolymer #4 |
| 1 | Ceric Sulfadiazine |
| 70 | Water |
| 15 | Isobutane (Propellant) |
| 100 | |

EXAMPLE 6

| | |
|---|---|
| 12 | Copolymer #5 |
| 2 | Isopropyl Myristate |
| 1 | Lanolin |
| 75 | Water |
| 10 | Pentane (Propellant) |
| 100 | |

EXAMPLE 7

| | |
|---|---|
| 10 | Copolymer #6 |
| 2 | Isopropyl Palmitate |
| 1 | Dimethyl Polysiloxane |
| 62 | Water |
| 25 | Freon 115 Propellant |
| 100 | |

EXAMPLE 8

| | |
|---|---|
| 15 | Copolymer #1 |
| 3 | Glyceryl Stearate |
| 70 | Water |
| 12 | Freon C-318 Propellant |
| 100 | |

In the above Examples:

Copolymer #4 is a polyoxyethylene-polyoxypropylene block copolymer of the type shown in formula (II) above having a hydrophobe molecular weight of 3250 and containing oxyethylene groups in the amount of 50 percent of the total weight of the copolymer.

Copolymer #5 is a polyoxyethylene-polyoxypropylene block copolymer of the type shown in formula (III) above having a hydrophobe molecular weight of 3000 and containing oxyethylene groups in amount of 70 percent of the total weight of the molecule.

Copolymer #6 is a polyoxyethylene-polyoxypropylene block copolymer of the type shown in formula (II) above having a hydrophobe molecular weight 3250 and containing oxyethylene groups in amount of 80 percent of the total weight of the molecule.

The embodiments in which an exclusive privilege or property is claimed are defined as follows:

1. A pressurized composition in an aerosol container capable of forming a spray upon release of pressure therefrom which composition is a liquid inside the container and forms a gel on contact with living tissue comprising by weight about 45 to 90 percent water, 3 to 50 percent propellant and 7 to 20 percent of a polyoxyethylene-polyoxypropylene copolymer of the formula:

$$Y[(C_3H_6O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxypropylene groups is from about 3250 to 7500; and the value of m is such that the oxyethylene groups constitute about 45 to 90 percent by weight of the total compound and wherein the water/copolymer weight ratio is at least about 4.5:1.

2. The composition of claim 1 wherein Y is a residue of propylene glycol whereby the resulting compounds have the structure $HO(C_2H_4O)_m(C_3H_6O)_n(C_2H_4O)_mH$ wherein n has a value such that the molecular weight of the polyoxypropylene hydrophobe is about 3250 to 4500 and m is the the same as for claim 1.

3. The composition of claim 2 including about 0.05 to 5.0 percent by weight skin treatment agent.

4. The composition of claim 3 including about 1.0 to 20 percent of at least one additional adjuvant.

5. A pressurized composition in an aerosol container capable of forming a spray upon release of pressure therefrom, which composition is a liquid inside the container and forms a gel on contact with living tissue, comprising by weight about 35 to 90 percent water, 3 to 50 percent of a propellant which is a solvent for said composition and 7 to 25 percent of a polyoxyethylene-polyoxypropylene copolymer of the formaula:

$$Y[(C_3H_6O)_n(C_2H_4O)_mH]$$

wherein Y is the residue of a water-soluble organic compound containing therein x active hydrogen atoms; n is an integer; x is an integer greater than 1; the value of n and x are such that the molecular weight of the oxypropylene groups is from about 2250 to 7500; and the value of m is such that the oxyethylene groups constitute about 45 to 90 percent by weight of the compound.

6. The composition of claim 5 wherein Y is a propylene glycol whereby the resulting compounds have the structure $HO(C_2H_4O)_m(C_3H_6O)_n(C_2H_4O)_mH$ wherein n has a value such that the molecular weight of the polyoxypropylene hydrophobe is about 2250 to 4500 and m is the the same as for claim 1.

7. The composition of claim 6 including about 0.05 to 5.0 percent by weight skin treatment agent.

8. The composition of claim 7 including about 1.0 to 20.0 percent of at least one additional adjuvant.

9. A process for treating living skin comprising spraying a gel composition in liquid form onto living skin, whereby a gel is formed on contact therewith, said composition comprising by weight about 45 to 90 percent water, about 3.0 to 50 percent propellant and about 7 to 20 percent of a polyoxyethylene-polyoxypropylene copolymer of the formula $$Y[(C_3H_6O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxypropylene groups is from about 3250 to 7500; and the value of m is such that the oxyethylene groups constitute about 45 to 90 percent by weight of the compound and wherein the water/copolymer weight ratio is at least about 4.5:1.

10. A process for treating living skin comprising spraying a gel composition in liquid form onto living skin, whereby a gel is formed on contact therewith, said composition comprising by weight about 35 to 90 percent water, about 3.0 to 50 percent of a propellant which is a solvent for said composition and about 7 to 25 percent of a polyoxyethylene-polyoxypropylene copolymer of the formula $$Y[(C_3H_6O)_n(C_2H_4O)_mH]$$

wherein Y is the residue of a water-soluble organic compound containing therein x active hydrogen atoms; n is an integer; x is an integer greater than 1; the value of n and x are such that the molecular weight of the oxypropylene groups is from about 2250 to 7500; and the value of m is such that the oxyethylene groups constitute about 45 to 90 percent by weight of the compound.

* * * * *

UNITED STATES PATENT AND TRADEMARK OFFICE
CERTIFICATE OF CORRECTION

PATENT NO. : 4,534,959
DATED : August 13, 1985
INVENTOR(S) : Irving Rudolf Schmolka It is certified that error appears in the above-identified patent and that said Letters Patent is hereby corrected as shown below:

Claim 5, line 12, delete "formaula" and insert therefor -- formula.--

Signed and Sealed this

Twenty-fourth Day of December 1985

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,534,959

DATED : August 13, 1985

INVENTOR(S) : Irving Rudolf Schmolka

It is certified that error appears in the above-identified patent and that said Letters Patent is hereby corrected as shown below:

Claims 5 and 10, revise formula to read as follows:

$$Y\left[(C_3H_6O)_n(C_2H_4O)_mH\right]_x$$

Signed and Sealed this

Ninth Day of September 1986

[SEAL]

Attest:

DONALD J. QUIGG

Attesting Officer

Commissioner of Patents and Trademarks